(12) United States Patent
Ozawa et al.

(10) Patent No.: US 9,795,557 B2
(45) Date of Patent: Oct. 24, 2017

(54) COSMETIC COMPOSITION

(71) Applicant: SUMITOMO SEIKA CHEMICALS CO., LTD., Hyogo (JP)

(72) Inventors: Hitoshi Ozawa, Osaka (JP); Tsuyoshi Masuda, Himeji (JP); Yusuke Nishikawa, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 14/383,725

(22) PCT Filed: Mar. 13, 2013

(86) PCT No.: PCT/JP2013/056926
§ 371 (c)(1),
(2) Date: Sep. 8, 2014

(87) PCT Pub. No.: WO2013/137290
PCT Pub. Date: Sep. 19, 2013

(65) Prior Publication Data
US 2015/0030649 A1     Jan. 29, 2015

(30) Foreign Application Priority Data
Mar. 13, 2012  (JP) ................................ 2012-055990

(51) Int. Cl.
| | | |
|---|---|---|
| A61K 9/14 | (2006.01) | |
| A61K 8/87 | (2006.01) | |
| A61K 8/34 | (2006.01) | |
| A61Q 5/00 | (2006.01) | |
| A61Q 19/00 | (2006.01) | |
| A61K 8/04 | (2006.01) | |
| A61K 9/16 | (2006.01) | |

(52) U.S. Cl.
CPC .................. *A61K 8/87* (2013.01); *A61K 8/04* (2013.01); *A61K 8/34* (2013.01); *A61Q 5/00* (2013.01); *A61Q 19/00* (2013.01); *A61K 9/1694* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 5,563,233 A | 10/1996 | Reich et al. | |
| 5,932,200 A | 8/1999 | Reich et al. | |
| 6,756,329 B1 * | 6/2004 | Umino | D01F 6/90 |
| | | | 442/181 |
| 2005/0053571 A1 * | 3/2005 | Hanada | A61K 8/898 |
| | | | 424/70.122 |
| 2006/0263324 A1 | 11/2006 | Nguyen-Kim | |
| 2012/0094880 A1 * | 4/2012 | Ozawa | C08G 18/0895 |
| | | | 508/583 |
| 2013/0012677 A1 | 1/2013 | Ozawa et al. | |

FOREIGN PATENT DOCUMENTS

| | | | |
|---|---|---|---|
| JP | H06-271419 | 9/1994 | |
| JP | H08-283128 | 10/1996 | |
| JP | H09-48721 | 2/1997 | |
| JP | H09-48722 | 2/1997 | |
| JP | H10-316531 | 12/1998 | |
| JP | H11-507405 | 6/1999 | |
| JP | 2005-171145 A1 | 6/2005 | |
| JP | 2006-500456 A1 | 1/2006 | |
| JP | 2007-503495 A1 | 2/2007 | |
| JP | 2009-513763 A1 | 4/2009 | |
| JP | WO 2010150875 A1 * | 12/2010 | ......... C08G 18/0895 |
| JP | 2012-41318 A1 | 3/2012 | |
| WO | WO 96/40820 | 12/1996 | |
| WO | WO 2004/029125 A1 | 4/2004 | |
| WO | WO 2007/048766 A2 | 5/2007 | |
| WO | 2008/007046 A1 | 1/2008 | |
| WO | 2011/086980 A1 | 7/2011 | |
| WO | WO 2012/096124 A1 | 7/2012 | |

OTHER PUBLICATIONS

The extended European search report dated Nov. 3, 2015 for corresponding EP patent application No. 13761783.3.
European Patent Application No. 13761783.3: Office Action dated Apr. 28, 2017.
International Search Report for International Application No. PCT/JP2013/056926 dated Jun. 11, 2013.

* cited by examiner

*Primary Examiner* — Susan Tran
(74) *Attorney, Agent, or Firm* — Kratz, Quintos & Hanson, LLP

(57) ABSTRACT

The present invention provides a cosmetic composition that is stable, not sticky when used, has excellent moisture and smoothness, and maintains the effects for a long time without deterioration due to washing and/or sweating.

Specifically, the present invention provides a cosmetic composition that comprises: (i) a polyalkylene oxide-modified product obtained by reacting a polyalkylene oxide compound, a diol compound, and a diisocyanate compound; and (ii) water or a lower alcohol aqueous solution, wherein the cosmetic composition comprises 0.3 mass % or more polyalkylene oxide-modified product.

7 Claims, 3 Drawing Sheets

COSMETIC COMPOSITION

TECHNICAL FIELD

The present invention relates to a cosmetic composition. More specifically, the present invention relates to a cosmetic composition that comprises a polyalkylene oxide-modified product, is applied to the skin or hair, and maintains excellent sliding characteristics after drying.

BACKGROUND ART

Recently, there is an increased number of cosmetics promoting an excellent feel in usage with less stimulus to the skin and no stickiness, while exhibiting moisture, smoothness, and silkiness. Heretofore, cosmetics aiming to improve the feel in usage include a cosmetic comprising organic powder and alcohol (Patent Literature 1).

However, when a cosmetic thus obtained is stored for a long period of time, due to the sedimentation and agglomeration of the organic powder, it was necessary to re-distribute the organic powder before use. A method is proposed by which the sedimentation of organic powder is prevented by the combined use of a thickener to maintain the distributed state (Patent Literature 2). However, in such a method, because the thickener covers the circumference of the organic powder, silkiness is problematically reduced.

Furthermore, the organic powder used herein is a spherical general thermoplastic resin with less stimulus to the skin. Such organic powder has little compatibility with water; therefore, the organic powder tends to be undesirably detached without absorbing water content, such as sweat from the skin, after the cosmetic has been applied to the skin and dried, causing a problem in that the smooth effect does not last for a long time, etc.

In order to maintain the smooth effect, the use of porous, water-absorbable powder, such as corn starch, which easily absorbs water and is free from stickiness, is proposed (Patent Literature 3 and 4). However, even when such a powder is used, the applied powder is simply placed on the surface of the skin or hair (i.e., the object of the application); therefore, when the cosmetic is washed off with water, the powder peels off and the effect thereof is reduced. A cosmetic wherein a specific superabsorbent polymer is used as an organic powder is also suggested (Patent Literature 5). In this case, the amount of the water is suitably selected to formulate the cosmetic. The superabsorbent polymer used herein has an extremely high water absorption capability, and a large amount of gel-absorbed water adheres to the surface of the skin, hair, or the like. This makes it difficult to achieve a smooth feeling in use, and also causes problems in terms of durability.

Furthermore, a hair dressing composition, in which a specific polyalkylene oxide-modified product is used as a cosmetic, is also suggested (Patent Literature 6). However, the polyalkylene oxide-modified product washes off with sweat or the like; therefore, its effect cannot last long.

CITATION LIST

Patent Literature

[PTL 1] JPH06-271419
[PTL 2] JP2005-171145
[PTL 3] JPH09-48721
[PTL 4] JPH09-48722
[PTL 5] JPH10-316531
[PTL 6] JPH08-283128

SUMMARY OF INVENTION

Technical Problem

The present invention aims to provide a cosmetic composition that is stable, not sticky when used, and has excellent moisture and smoothness, whose effects will last for a long period of time without deterioration due to washing and/or sweating.

Solution to Problem

The present inventors conducted extensive research to solve the above problems and found that when a composition comprising a specific polyalkylene oxide-modified product, and water or a lower alcohol aqueous solution is applied to the skin, hair, or the like and then dried, its mean coefficient of friction (MIU), which is an index showing difficulty in sliding on the surface, becomes small, and its deviation in mean coefficient of friction (MMD), which is an index showing surface roughness, becomes small; thus exhibiting excellent stability. Therefore, excellent moisture and smoothness can be maintained with no stickiness. The inventors conducted further research and have accomplished the present invention.

More specifically, the present invention encompasses the following subject matter:

Item 1.
A cosmetic composition comprising:
(i) a polyalkylene oxide-modified product obtained by reacting a polyalkylene oxide compound, a diol compound, and a diisocyanate compound; and
(ii) water or a lower alcohol aqueous solution; the cosmetic composition comprising 0.3 mass % or more (preferably 0.3 to 7.5 mass %) polyalkylene oxide-modified product.

Item 2-1.
The cosmetic composition according to Item 1, wherein the polyalkylene oxide compound comprises at least one member selected from the group consisting of polyethylene oxide, polypropylene oxide, polybutylene oxide, ethylene oxide/propylene oxide copolymer, ethylene oxide/butylene oxide copolymer, propylene oxide/butylene oxide copolymer, and ethylene oxide/propylene oxide/butylene oxide copolymer.

Item 2-2.
The cosmetic composition according to Item 1, wherein the polyalkylene oxide compound is at least one member selected from the group consisting of polyethylene oxide, polypropylene oxide, polybutylene oxide, ethylene oxide/propylene oxide copolymer, ethylene oxide/butylene oxide copolymer, propylene oxide/butylene oxide copolymer, and ethylene oxide/propylene oxide/butylene oxide copolymer.

Item 3-1.
The cosmetic composition according to any one of Items 1 to 2-2, wherein the diol compound comprises at least one member selected from the group consisting of ethylene glycol, diethylene glycol, triethylene glycol, tetraethylene glycol, propylene glycol, dipropylene glycol, trimethylene glycol, 1,3-butanediol, 2,3-butanediol, 1,4-butanediol, 1,5-pentanediol, 1,6-hexanediol, and 1,9-nonanediol.

Item 3-2.
The cosmetic composition according to any one of Items 1 to 2-2, wherein the diol compound is at least one member selected from the group consisting of ethylene glycol, diethylene glycol, triethylene glycol, tetraethylene glycol, propylene glycol, dipropylene glycol, trimethylene glycol, 1,3-butanediol, 2,3-butanediol, 1,4-butanediol, 1,5-pentanediol, 1,6-hexanediol, and 1,9-nonanediol.

Item 4-1.

The cosmetic composition according to any one of Items 1 to 3-2, wherein the diisocyanate compound comprises at least one member selected from the group consisting of 4,4'-diphenylmethane diisocyanate (MDI), 1,6-hexamethylene diisocyanate (HDI), dicyclohexylmethane-4,4'-diisocyanate (HMDI), 3-isocyanate methyl-3,5,5-trimethyl cyclohexyl isocyanate (IPDI), 1,8-dimethylbenzole-2,4-diisocyanate, and 2,4-tolylene diisocyanate (TDI).

Item 4-2.

The cosmetic composition according to any one of Items 1 to 3-2, wherein the diisocyanate compound is at least one member selected from the group consisting of 4,4'-diphenylmethane diisocyanate (MDI), 1,6-hexamethylene diisocyanate (HDI), dicyclohexylmethane-4,4'-diisocyanate (HMDI), 3-isocyanate methyl-3,5,5-trimethyl cyclohexyl isocyanate (IPDI), 1,8-dimethylbenzole-2,4-diisocyanate, and 2,4-tolylene diisocyanate (TDI).

Item 5.

The cosmetic composition according to any one of Items 1 to 4-2, wherein the polyalkylene oxide-modified product has a median diameter of 30 to 150 µm.

Item 6.

The cosmetic composition according to any one of Items 1 to 5, wherein the polyalkylene oxide-modified product has a water absorption capability of 10 to 40 g/g.

Item 7.

The cosmetic composition according to any one of Items 1 to 6, wherein the polyalkylene oxide-modified product has a water elution amount of 10 to 40 mass %.

Item 8.

A cosmetic obtainable using the cosmetic composition of any one of Items 1 to 7.

Item 9.

Use of a composition as a cosmetic, the composition comprising:

(i) a polyalkylene oxide-modified product obtained by reacting a polyalkylene oxide compound, a diol compound, and a diisocyanate compound, and (ii) water or a lower alcohol aqueous solution, the cosmetic composition comprising 0.3 mass % or more (preferably 0.3 to 7.5 mass %) polyalkylene oxide-modified product.

Advantageous Effects of Invention

The cosmetic composition of the present invention exhibits excellent stability and a good feel in usage, with no stickiness to the skin, hair, or the like when applied, exhibits smoothness when dried, and the effects thereof stably remain even after washing with water. Utilizing such characteristics, the cosmetic composition can be preferably used for washing, activating, skin conditioning, hair styling, or protection of the face, hands, neck, hair, or other parts of the body.

BRIEF DESCRIPTION OF DRAWINGS

FIG. 1 shows the measurement using a piano wire sensor while placing a sample on a movable table moving right and left at a speed of 10 mm/sec.

DESCRIPTION OF EMBODIMENTS

Figure 1:
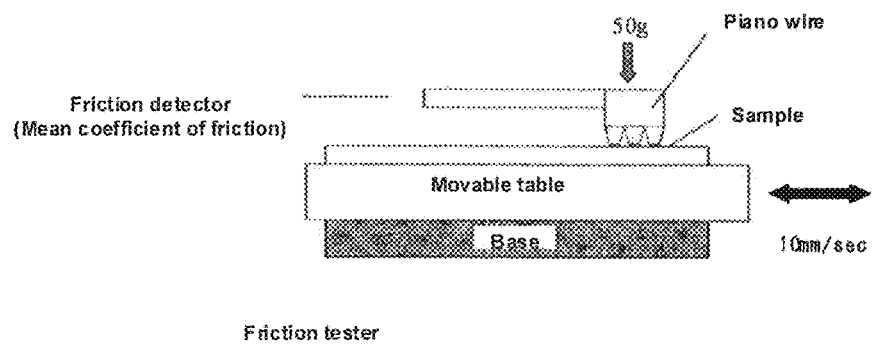
FIG. 1 is a schematic diagram illustrating a friction coefficient monitor.

The composition of the present invention comprises a specific polyalkylene oxide-modified product, and water or a lower alcohol aqueous solution. The polyalkylene oxide-modified product is a compound obtained by reacting (polymerizing) a polyalkylene oxide compound, a diol compound, and a diisocyanate compound. The cosmetic composition of the present invention contains the polyalkylene oxide-modified product in water or a lower alcohol aqueous solution. The cosmetic composition of the present invention may be in the form of a liquid, a gel, a cream or the like, but is preferably in the form of a liquid cosmetic composition.

The cosmetic composition of the present invention comprises a polyalkylene oxide-modified product in an amount of 0.3 mass % or more, preferably about 0.3 to 7.5 mass %, more preferably about 0.4 to 7.0 mass %, further preferably about 0.4 to 6.0 mass %, yet more preferably about 0.5 to 5.0 mass %, and particularly preferably about 0.5 to 4.0 mass %. When the content of the polyalkylene oxide-modified product is less than 0.3 mass %, the excellent feel in usage (in particular, smoothness) may not be obtainable when the final cosmetic composition is used. Here, the unit of the content of polyalkylene oxide-modified product "mass %" is "mass/mass %."

The polyalkylene oxide-modified product is preferably water absorbable (i.e., having water absorption capability). When the polyalkylene oxide-modified product is water absorbable, its water absorption capability is preferably 10 to 40 g/g, and more preferably 15 to 35 g/g. When the water-absorbable polyalkylene oxide-modified product has a water absorption capability of 10 g/g or more, smoothness after application and drying can be preferably obtained. Furthermore, when the polyalkylene oxide-modified product has a water absorption capability of 40 g/g or less, the durability of the resulting cosmetic after application can be improved. In the present invention, the expression "water absorption capability" indicates the value obtained below. That is, 1 g of polyalkylene oxide-modified product is weighed (A[g]), and immersed in 100 mL of ion exchange water at room temperature (22° C.) for 24 hours to be gelated. The gel thus obtained is subjected to filtration using a wire sieve with 200 mesh (diameter of openings: 75 µm), and the mass (B[g]) of the filtered out substance (residue) (i.e., the mass of the gel) is measured. The water absorption capability is the value calculated using the following equation (in the equation, because A is 1, the water absorption capability is the value of B).

Water absorption capability (g/g)=$B/A=B/1=B$

The water elution amount of the polyalkylene oxide-modified product is preferably 10 to 40 mass %, and more preferably 15 to 35%. When the polyalkylene oxide-modified product has a water elution amount of 10 mass % or more, the resulting cosmetic is capable of exhibiting excellent smoothness after application and drying. When the polyalkylene oxide-modified product has a water elution amount of 40 mass % or less, the sustainability when washing may be further improved. The water elution amount in the present invention is the value obtained by the following equation. In the equation, (C[g]) is the mass of the gel weighed after being subjected to the above water absorption capability measurement, followed by drying with a hot air dryer at 50° C. for 8 hours.

$$\text{Water elution amount (mass \%)} = \{(A-C)/A\} \times 100 = 100(1-C)$$

Examples of the polyalkylene oxide compound include polyethylene oxide, polypropylene oxide, polybutylene oxide, ethylene oxide/propylene oxide copolymer, ethylene oxide/butylene oxide copolymer, propylene oxide/butylene oxide copolymer, and ethylene oxide/propylene oxide/butylene oxide copolymer. The polyalkylene oxide compound may be used singly or in a combination of two or more. Here, the symbol "/" is used to indicate that it is a copolymer of each oxide. For example, the ethylene oxide/propylene oxide copolymer is a copolymer of ethylene oxide and propylene oxide.

There is no particular limitation, and the polyalkylene oxide compound preferably has a number average molecular weight of 5,000 to 50,000, and more preferably has a number average molecular weight of 10,000 to 30,000. When the polyalkylene oxide compound has a number average molecular weight of 5,000 or more, the smoothness attained by applying and drying the cosmetic composition can be further improved. When the polyalkylene oxide compound has a number average molecular weight of 50,000 or less, the durability of the resulting cosmetic composition may be further improved.

Here, the number average molecular weight is a value obtained by a measurement method described below. The number average molecular weight measurement method: A dimethylformamide solution having a polyalkylene oxide-modified product, concentration of 1 mass % is prepared and then subjected to measurement using high-performance liquid chromatography. The measurement of a molecular weight marker (polyethylene oxide), whose molecular weight is known, is performed under the same conditions to prepare a calibration curve to obtain the number average molecular weight (Mn). Note that the measurement conditions are as follows.

Measuring equipment: HLC-8220 (manufactured by Tosoh Corporation)

Column: manufactured by Tosoh Corporation; Model name: TSK GEL Multipore HXL-M

Column temperature: 40° C.

Eluent: dimethylformamide

Flow rate: 0.6 mL/min

Among the above, a polyalkylene oxide compound containing 90 mass % or more of an ethylene oxide group is preferable, and a polyalkylene oxide compound containing 95 mass % or more of an ethylene oxide group is more preferable. When the content of the ethylene oxide group is 90 mass % or more, the stickiness of the cosmetic composition after application and drying can be desirably suppressed.

Examples of the diol compound include ethylene glycol, diethylene glycol, triethylene glycol, tetraethylene glycol, propylene glycol, dipropylene glycol, trimethylene glycol, 1,3-butanediol, 2,3-butanediol, 1,4-butanediol, 1,5-pentanediol, 1,6-hexanediol, and 1,9-nonanediol. Among these diol compounds, from the viewpoint that the resulting cosmetic composition obtained using the polyalkylene oxide-modified product becomes more compatible to skin, hair, or the like, ethylene glycol and/or 1,4-butanediol are/is preferably used. These diol compounds may be used singly or in a combination of two or more.

The amount of the diol compound is preferably 0.8 to 2.5 mol and more preferably 1.0 to 2.0 mol, per 1 mol of the polyalkylene oxide compound. Note that the number of moles of a polyalkylene oxide compound can be obtained by dividing the mass thereof by its number average molecular weight.

The diisocyanate compound is not limited as long as it comprises two isocyanate groups (—NCO) in the same molecule, and examples thereof include 4,4'-diphenylmethane diisocyanate (MDI), 1,6-hexamethylene diisocyanate (HDI), dicyclohexylmethane-4,4'-diisocyanate (HMDI), 3-isocyanate methyl-3,5,5-trimethyl cyclohexyl isocyanate (IPDI), 1,8-dimethylbenzole-2,4-diisocyanate, and 2,4-tolylene diisocyanate (TDI). Among these diisocyanate compounds, dicyclohexylmethane-4,4'-diisocyanate (HMDI) and 1,6-hexamethylene diisocyanate (HDI) are preferably used. These diisocyanate compounds may be used singly or in a combination of two or more.

The proportions of the polyalkylene oxide compound, diol compound, and diisocyanate compound used are each selected so that the molar ratio of the moles of the isocyanate groups of the diisocyanate compound relative to the total moles of the terminal hydroxyl groups of the polyalkylene oxide compound and the hydroxyl groups of the diol compound [R value=(—NCO group/—OH group)] is preferably about 0.7 to 1.2, and more preferably about 0.8 to 1.05. When the R value is 0.7 or more, the durability of a cosmetic composition comprising the resulting polyalkylene oxide-modified product can be further improved. When the R value is 1.2 or less, the water absorption capability of the resulting polyalkylene oxide-modified product is improved and the smoothness of the cosmetic composition comprising the polyalkylene oxide-modified product can be further improved.

The polyalkylene oxide compound, diol compound, and diisocyanate compound may be reacted by a known method. For example, this includes a method in which these compounds are reacted by dissolution or dispersion in a reaction solvent, such as toluene, xylene, or dimethylformamide; and a method in which these compounds in a form of powder or solid are uniformly mixed and then heated to a predetermined temperature to react them. From the viewpoint of industrial practice, a preferable method is such that each material is continuously supplied in a molten state and reacted while mixing in a multi-screw extruder. In this case, the reaction temperature is preferably 70 to 210° C.

When the polyalkylene oxide-modified product is prepared, a catalyst may be added to the reaction system in order to facilitate the reaction. For example, as a catalyst, a suitable amount of triethylamine, triethanolamine, dibutyltin dilaurate, dioctyltin dilaurate, tin 2-ethylhexanoate, or triethylenediamine may be added.

This method allows a polyalkylene oxide-modified product to be obtained. According to this method, a polyalkylene oxide-modified product is usually obtained in a form such as a pellet, sheet, or film. Such a polyalkylene oxide-modified product is preferably pulverized/crashed with a grinder or the like, and then used as the cosmetic composition of the present invention. The pulverization method is not particularly limited, and freeze-pulverization is preferable in order to prevent the fusion that occurs due to shear heating while grinding. Freeze-pulverization may be performed using, for example, liquid nitrogen.

The intermediate diameter (which may also be referred to as median diameter or 50% particle diameter) of the pulverized polyalkylene oxide-modified product is preferably 30 to 150 μm, and more preferably 50 to 100 μm. More specifically, the polyalkylene oxide-modified product is suitably used as the cosmetic composition of the present invention, preferably as a powder having a median diameter in the aforementioned range. When the median diameter is 30 μm or more, the durability may be improved. Furthermore, when the median diameter is 150 μm or less, the resistance at the time of application is less likely to become large, and more preferably attains smoothness. In the present invention, the median diameter refers to the median diameter obtained by a dry sieving method (JIS Z8815). More specifically, the median diameter refers to that determined by weighing 50 g of polyalkylene oxide-modified product and sieving it using JIS standard sieves (JIS Z8801), followed by weighing the amount that remains in each sieve.

An example of the lower alcohol aqueous solution includes a mixed solution of a lower alcohol and water. The content of the lower alcohol is not particularly limited and, for example, can be 0 to 95 mass % (more specifically, for example, 5, 10, 15, 20, 25, 30, 35, 40, 45, 50, 55, 60, 65, 70, 75, 80, 85, or 90 mass %). When the cosmetic composition of the present invention does not contain a lower alcohol (i.e., when water is used without a lower alcohol), the drying speed after application to the skin, hair, or the like slows down slightly, but it is advantageous because the stimulation decreases. In contrast, when the cosmetic composition of the present invention uses a lower alcohol aqueous solution, in particular, when the lower alcohol aqueous solution contains a lower alcohol in an amount of 50 mass % or more, the drying speed of the resulting cosmetic composition tends to increase, which is preferable in this respect.

Examples of lower alcohols include $C_{1-6}$ alkyl alcohol and benzyl alcohol. Specific examples thereof include monovalent alcohols, such as methanol, ethanol, propanol, isopropanol, butanol, and benzyl alcohol. Among these, ethanol, propanol, and isopropanol are more preferable because they are highly safe and have excellent volatility. These lower alcohols may be used singly or in a combination of two or more.

An example of the method for producing the cosmetic composition of the present invention is such that the polyalkylene oxide-modified product (powder) is mixed with a predetermined amount of water or a lower alcohol aqueous solution at room temperature, and then dispersed (and subjected to liquid adsorption when the polyalkylene oxide-modified product is a water-absorbable polyalkylene oxide-modified product). The polyalkylene oxide-modified product is dissolved when heated, so a more transparent cosmetic composition can be obtained. The mixing method is not particularly limited and may be performed by employing a known method. For example, mixing may be performed using a propeller mixer, a high speed mixer, a homogenizer, etc.

The cosmetic composition of the present invention may contain other components as long as it does not adversely affect the effects of the present invention. As such other components, those generally used for cosmetics may be added. Specific examples of such components include glycerol, glycol, sorbitol, dipropylene glycol, and polyethylene glycol. These components are preferably added, in particular, when the cosmetic composition of the present invention is used as a moisturizer. Furthermore, aluminum hydroxychloride, tannic acid, zinc sulfate, zinc oxide, etc., colorants, surfactants (anionic, nonionic, amphoteric or cationic), other flavoring agents, antioxidants, ultraviolet absorbers, plant extracts, and the like may also be added. These components are preferably added when the cosmetic composition of the present invention is used as an antiperspirant.

The cosmetic composition of the present invention may be used as a cosmetic without any modification, or may also be used as a cosmetic (cosmetic product) by being combined with carriers and the like that are generally applicable to cosmetics. Specific examples of cosmetics include skin-care products, makeup products, hair-care products, body-care products, and fragrances. The form of the cosmetic is not particularly limited, and examples thereof include a facial powder foundation, a facial liquid foundation, a milky lotion, a face lotion, a liquid cosmetic, a facial pack, a cleansing foam, a shampoo, a hair conditioner, a hair set agent, and an emollient cream. These cosmetic products can be produced by an ordinary method.

EXAMPLES

The present invention is explained in detail below with reference to Examples and Comparative Examples. However, the scope of the present invention is not limited by these Examples.

Evaluation Method

The polyalkylene oxide-modified product and polyacrylate crosslinked product produced in the Production Examples were measured in terms of (1) water absorption capability, (2) water elution amount, and (3) median diameter by the methods described below. Furthermore, the cosmetics used in the Examples described below were measured in terms of (4) sliding characteristics and (5) stability when applied by the method described below.

(1) Water Absorption Capability

The water absorption capability of the polyalkylene oxide-modified product was measured by the following method.

1 g (A[g]) of polyalkylene oxide-modified product was weighed and then immersed in 100 mL of ion exchange water, which was measured using a 200-mL beaker, at room temperature (22° C.) for 24 hours to gelate it. Thereafter, the gel was filtered using a 200-mesh (pore diameter: 75 μm) wire sieve, its mass (B[g]) was measured, and the water absorption capability thereof was measured using the following equation:

$$\text{Water absorption capability (g/g)} = B/A = B$$

(2) Water Elution Amount

After being subjected to the water absorption capability measurement, the gel was dried by hot air of 50° C. for 8 hours. The mass of the result was weighed (C[g]), and the water elution amount was calculated by the following equation.

$$\text{Water elution amount (mass \%)} = \{(A-C)/A\} \times 100 = 100(1-C)$$

(3) Median Diameter

The median diameter of the sample was obtained by a dry sieving method (JIS Z8815). Specifically, 50 g of the obtained sample was weighed, the weighed sample was sieved using a JIS standard sieve (JIS Z8801) and then the amount in each sieve was weighed. Based on the results, the median diameter at which the cumulative sieving mass fraction becomes 50% was obtained.

(4) Sliding Characteristics 0.1 mL of each cosmetic obtained in the Examples and Comparative Examples was dropped onto artificial leather (manufactured by Idemitsu Techno Ltd., Model name: Sapurare) cut into pieces having a size of 2 cm (W)×5 cm (L), the dropped cosmetic was rubbed in to the entire surface of the artificial leather pieces with the pad of a finger and then dried. Thereafter, using a friction tester (Kato Tech Co., Ltd., Model name: KES-SE), under the following test conditions, the coefficient of friction μ was monitored. Thereafter, the mean coefficient of friction (MIU) and deviation in mean coefficient of friction (MMD) were obtained.

Friction Tester Conditions
 Sensor: 10-mm-square piano wire
 Load: 50 g
 Speed: 10 mm/second FIG. 1 shows a schematic diagram illustrating the monitoring process for the friction coefficient.

(i) Mean Coefficient of Friction (MIU)

The mean coefficient of friction correlates with the difficulty in sliding felt when rubbing the surface of the leather (conversely, the ease of sliding). When this value becomes large, it becomes more difficult to slide.

Figure 2:
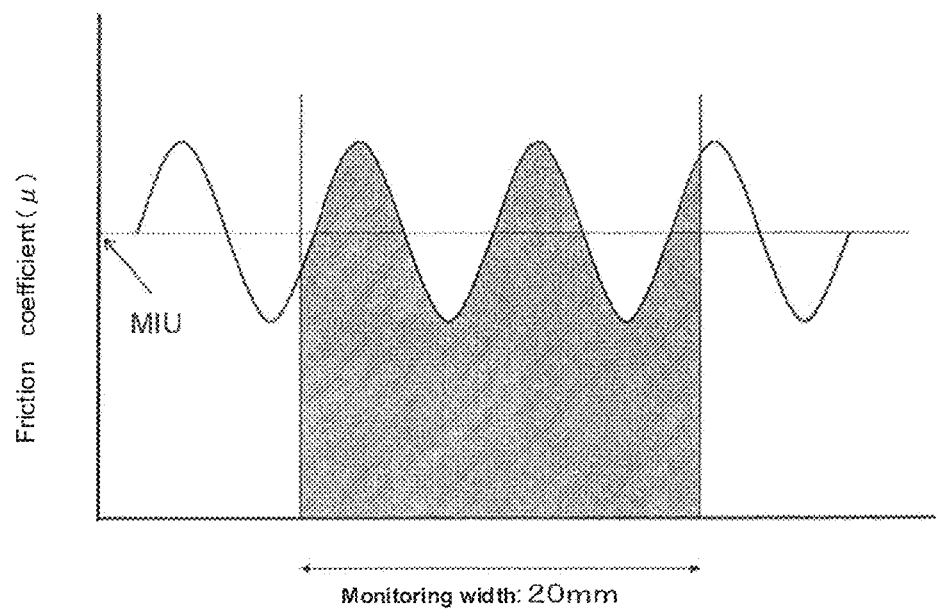
FIG. 2 is a schematic diagram illustrating the process of obtaining an mean coefficient of friction (MIU) using the results of monitoring the friction coefficient.

FIG. 2 shows a schematic diagram illustrating the method for obtaining the mean coefficient of friction (MIU) based on the results of monitoring the coefficient of friction μ.

As shown in FIG. 2, the coefficient of friction μ of the surface is monitored by scanning the surface of the measurement sample. Subsequently, in a monitoring width of 20 mm, the coefficient of friction μ is integrated (shadow area of FIG. 2). By dividing the integrated value by the monitoring width (20 mm), the mean coefficient of friction (MIU) can be obtained.

When the MIU value is 0.3 or less, the sample is evaluated as having excellent sliding characteristics. The measurement revealed that the MIU of the artificial leather itself was 0.37.

(ii) Deviation in Mean Coefficient of Friction (MMD)

The deviation in mean coefficient of friction correlates with the roughness felt when rubbing the surface of the leather (conversely, the smoothness). When this value becomes large, it becomes rougher.

Figure 3:
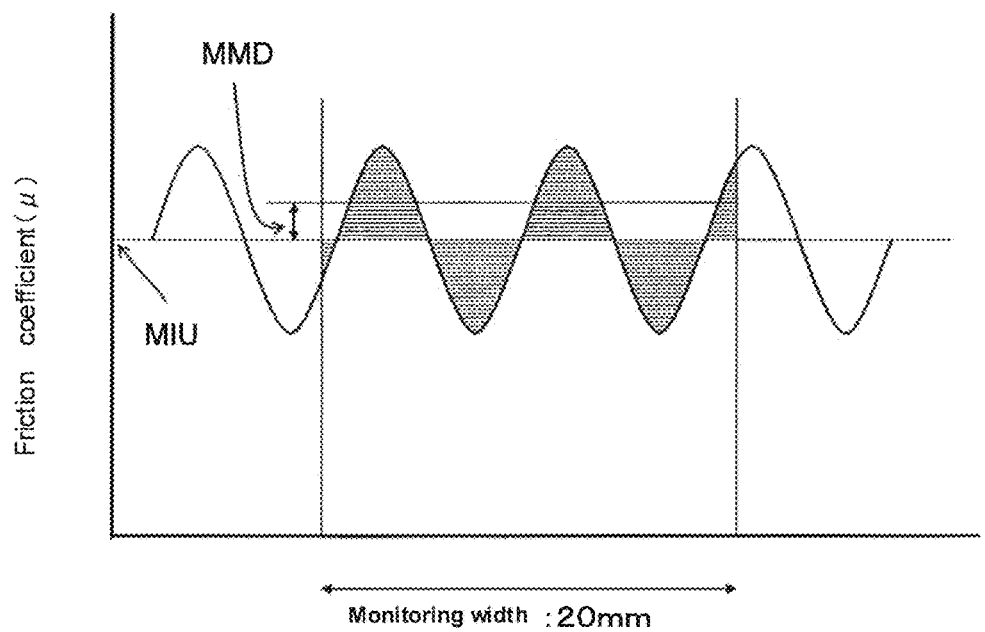
FIG. 3 is a schematic diagram illustrating the process of obtaining a deviation in mean coefficient of friction (MMD) using the results of monitoring the friction coefficient.

FIG. 3 shows a schematic diagram illustrating how the deviation in mean coefficient of friction (MMD) is obtained based on the results of monitoring the coefficient of friction.

In the monitoring width of 20 mm, the absolute value of the difference between an mean coefficient of friction (MIU) and a coefficient of friction μ is integrated as shown in FIG. 3 (shadow area of FIG. 3). By dividing the integrated value by the monitoring width (20 mm), the deviation in mean coefficient of friction (MMD) can be obtained. As is clear from the obtainment method described above, MMD can be called an index indicating the degree of variation of MIU. Therefore, it can also be said that MMD is an index indicating the smoothness of the surface.

In particular, when the value of MMD is 0.015 or less, the surface has excellent smoothness. Measurement revealed that the artificial leather itself had an MMD of 0.02.

Furthermore, in terms of the sliding characteristics, an experiment under running water (a durability experiment) was also conducted under the conditions described below.

(iii) Experiment Under Running Water (Durability Experiment)

Artificial leather into which 0.1 mL of cosmetic had been rubbed was placed under running tap water for two minutes while being tilted 300 relative to the horizontal plane, with the tap water flowing directly thereon at a rate of 100 mL/min. The water remaining on the surface of the artificial leather was then wiped off with a paper towel. Thereafter, the sheet was dried by placing it in an oven having a temperature of 50° C. for 1 hour. The above procedure was repeated five times. Then, the mean coefficient of friction (MIU) and deviation in mean coefficient of friction (MMD) were obtained by monitoring the coefficient of friction under the same conditions as described above.

(5) Stability 100 g of each cosmetic obtained in each of the Examples and Comparative Examples was placed into a hard glass sample vial. The sample vials were placed on the south side of an exposure test fence mounted on the roof of a two-story building to be exposed to sunlight under fine weather for ten days. The viscosity before and after the exposure was measured under the conditions described below.

Viscosity Measurement Conditions
 Equipment used: Brookfield viscometer (manufactured by Shibaura Semtech Co. Ltd., Model name: VDH2)
 Measurement temperature: 25°
 Rotor: No. 6
 Rotational speed: 20 rpm Hereunder, Production Examples are described in detail. In the Production Examples, the R value indicates the value of (the number of moles of —NCO groups/the number of moles of —OH group). In terms of an extruder, L/D indicates the ratio of the effective length of the screw (L) to the screw diameter (D).

Production Example 1: Production of Polyalkylene Oxide-Modified Product

In a storage tank A equipped with a stirrer maintained at 80° C., 100 parts by mass of fully dehydrated polyethylene oxide having a number average molecular weight of 20,000, 0.9 parts by mass of 1,4-butanediol, and 0.1 parts by mass of dioctyltin dilaurate were placed at the above proportions, followed by stirring under a nitrogen gas atmosphere to obtain a uniform mixture. Dicyclohexyl methane-4,4'-diisocyanate was poured into a separate storage tank B maintained at 30° C. and then stored under a nitrogen gas atmosphere.

Using a metering pump, the mixture in the storage tank A and the dicyclohexyl methane-4,4'-diisocyanate in the storage tank B were continuously fed to a twin screw extruder having a temperature set at 110 to 140° C. at a respective speed of 500 g/min and 19.4 g/min (R value=1.00), and allowed to react while being mixed inside the extruder. Strands thereof were output from the exit of the extruder, and pelletized by a pelletizer, thereby obtaining a polyalkylene oxide-modified product.

The polyalkylene oxide-modified product thus obtained had a water absorption capability of 25 g/g, and a water elution amount of 19 mass %. The pellets thus obtained were immersed in liquid nitrogen and then pulverized into powder having a median diameter of 60 μm.

Production Example 2: Production of Polyalkylene Oxide-Modified Product

An ethylene oxide/propylene oxide (mass ratio: 90/10) copolymer having a number average molecular weight of 15,000 and ethylene glycol heated to 40° C. were fed to a single screw extruder (L/D=40, temperature setting: 90° C.) having a diameter of 40 mm at a respective speed of 250 g/min and 2.1 g/min. Here, the diameter means the diameter of the screw.

The resulting mixture (discharged in a uniform molten state and confirmed to have been mixed at the content ratio by HPLC analysis) obtained from the discharge port was continuously fed to a twin screw extruder (L/D=41.5) having a diameter of 30 mm through the opening of a hopper (temperature setting: 80° C.). At the same time, dioctyltin dilaurate was fed into the opening of the hopper of the twin screw extruder at a speed of 0.5 g/min.

Furthermore, to the screw barrel portion located downstream of the opening of the hopper of the twin screw extruder, dicyclohexyl methane-4,4'-diisocyanate adjusted to 30° C. was also fed at a speed of 12.4 g/min (R value=0.95), and then allowed to continuously react under a nitrogen atmosphere (preset temperature: 180° C.). The resulting strands obtained from the exit of the twin screw extruder were cooled, and pelletized using a pelletizer, thereby obtaining a polyalkylene oxide-modified product.

The polyalkylene oxide-modified product thus obtained had a water absorption capability of 20 g/g and a water elution amount of 15 mass %. The pellets thus obtained were immersed in liquid nitrogen and pulverized into powder having a median diameter of 100 μm.

Production Example 3: Production of
Acrylate-Based Water-Soluble Polymer

A 1,000-mL five necked cylindrical round bottom flask equipped with a reflux condenser, a dropping funnel, a nitrogen gas introduction pipe as well as a stirrer and an impeller was prepared. 340 g of n-heptane was poured into this flask. 0.92 g of HLB3 sucrose stearate (manufactured by Mitsubishi-Kagaku Foods Corporation, Ryoto sugar ester S-370) and 0.92 g of a maleic anhydride-modified ethylene-propylene copolymer (manufactured by Mitsui Chemicals, Inc., Hi-wax 1105A) were added thereto. The mixture was heated to 80° C. while stirring, to dissolve the surfactant, and then the solution was cooled to 55° C.

On the other hand, 92 g (1.02 mol) of an 80 mass % aqueous solution of acrylic acid was placed into a 500-mL Erlenmeyer flask, and 54.5 g (0.41 mol) of a 30 mass % aqueous solution of sodium hydroxide was added dropwise thereto while cooling from the outside to perform neutralization of 40 mol %. Thereafter, as a radical initiator, 1.15 g of a 2.0 mass % aqueous solution of 2,2'-azobis(2-amidino-propane)dihydrochloride, 0.92 g of a 1.0 mass % aqueous solution of sodium hypophosphite monohydrate, and 60 g of ion exchange water were added thereto and dissolved, thereby preparing a monomer aqueous solution.

The total amount of this monomer aqueous solution was poured into the cylindrical round bottom flask. The flask was immersed in a water bath of 60° C. to raise the temperature of the content to 58° C. Thereafter, the atmosphere in the system was replaced with nitrogen, followed by a polymerization reaction. Thirty minutes later, the mixture reached the peak temperature of 79° C. Therefrom, the reaction was allowed to continue while being immersed in a water bath of 60° C. for 0.5 hours. The temperature of the liquid inside of the flask after 0.5 hours was 59° C. The resulting polymerized slurry liquid was cooled to 30° C. to obtain samples, the amount of the remaining monomers was obtained using HPLC to calculate the polymerization rate. The polymerization rate was 96 mol %.

After the completion of the polymerization, the polymerized slurry liquid was heated to 125° C. in an oil bath, and 106 g of water was removed from the system by azeotropic distillation of water and n-heptane while refluxing n-heptane. Furthermore, n-heptane in the system was removed by distillation and then dried, thereby obtaining 86.1 g of acrylate-based water-soluble polymer. The acrylate-based polymer thus obtained was classified to have a median diameter of 50 μm. The resulting acrylate-based polymer was water soluble, and did not exhibit water absorbency. More specifically, the polymer obtained was an acrylate-based water-soluble polymer.

Production Example 4: Production of
Acrylate-Based Water-Absorbable Polymer 550 mL of n-heptane was poured into a 1-L four necked cylindrical round bottom flask equipped with a stirrer, a reflux condenser, and a nitrogen gas introduction pipe. 1.38 g of hexaglyceryl monobeherate having an HLB of 13.1 (surfactant: manufactured by Nippon Oil & Fats Co., Ltd.: Product name: Nonion GV-106) was added thereto and then dispersed therein. The mixture was heated to 50° C. to dissolve the surfactant, and then the solution was cooled to 30° C.

A 500-mL Erlenmeyer flask was separately prepared, and 92 g of an 80 mass % aqueous solution of acrylic acid was placed therein. While cooling the flask from the outside, 152.6 g of a 20.1 mass % of sodium hydroxide aqueous solution was added thereto dropwise to perform neutralization of 75 mol %. Thereafter, 0.11 g of potassium persulfate and 0.019 g of ethylene glycol diglycidyl ether, as a cross-linking agent, were further added thereto and then dissolved, thereby obtaining a partially neutralized acrylic acid aqueous solution.

Subsequently, the total amount of the partially neutralized acrylic acid aqueous solution was poured into the four necked cylindrical round bottom flask and dispersed therein. The atmosphere in the system was replaced with nitrogen and the temperature of the system was raised. While maintaining the bath temperature at 70° C., a polymerization reaction was performed for 3 hours.

After the completion of the polymerization reaction, the slurry containing the acrylate-based water-absorbable polymer was dried at 120° C. for 2 hours, thereby obtaining 191.2 g of acrylate-based water-absorbable polymer.

The acrylate-based water-absorbable polymer thus obtained was classified so as to have a median diameter of 100 μm. Furthermore, the acrylate-based water-absorbable polymer had a water absorption capability of 550 [g/g].

Example 1

Powder of the polyalkylene oxide-modified product obtained in Production Example 1 was dispersed in water so as to have a concentration of 3 mass % at ordinary temperature, obtaining a cosmetic composition.

Example 2

Powder of the polyalkylene oxide-modified product obtained in Production Example 1 was dispersed in a 90 mass % of ethanol aqueous solution so as to have a concentration of 3 mass % at 20° C., obtaining a cosmetic composition.

Example 3

Powder of the polyalkylene oxide-modified product obtained in Production Example 2 was dispersed in a 65 mass % of isopropanol aqueous solution so as to have a concentration of 0.5 mass % at ordinary temperature, obtaining a cosmetic composition.

Example 4

Powder of the polyalkylene oxide-modified product obtained in Production Example 2 was dispersed in an 80 mass % of propanol aqueous solution so as to have a concentration of 1.5 mass % at 20° C., obtaining a cosmetic composition.

Comparative Example 1

Powder of the polyalkylene oxide-modified product obtained in Production Example 1 was dispersed in water so as to have a concentration of 0.1 mass % at 20° C., obtaining a cosmetic composition.

Comparative Example 2

The acrylate-based water-absorbable polymer obtained in Production Example 3 was dispersed in a 90 mass % ethanol aqueous solution so as to have a concentration of 3 mass % at 20° C., obtaining a cosmetic composition.

Comparative Example 3

The acrylate-based water-absorbable polymer obtained in Production Example 4 was dispersed in water so as to have a concentration of 3 mass % at 20° C., obtaining a cosmetic composition.

Figure 4A:
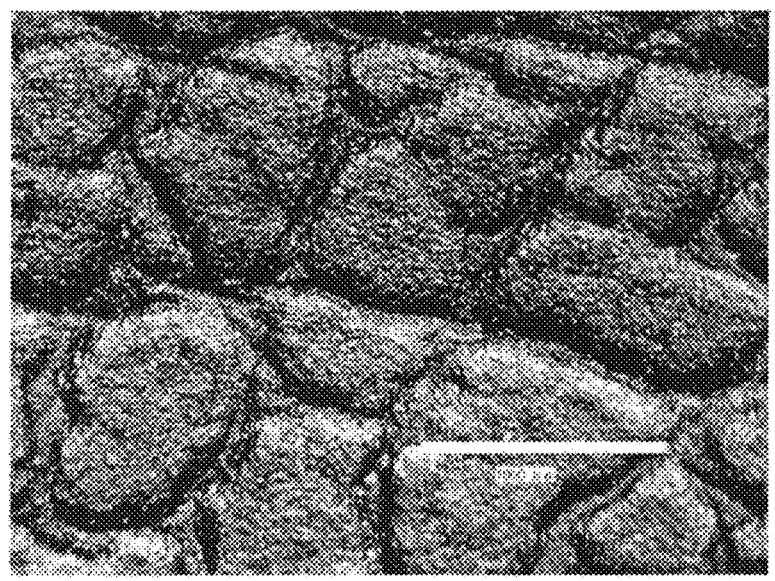
FIG. 4a is an enlarged view of the surface of the artificial leather used to evaluate sliding characteristics. In the figure, the white bar indicates a length of 1,000 µm.
Figure 4B:
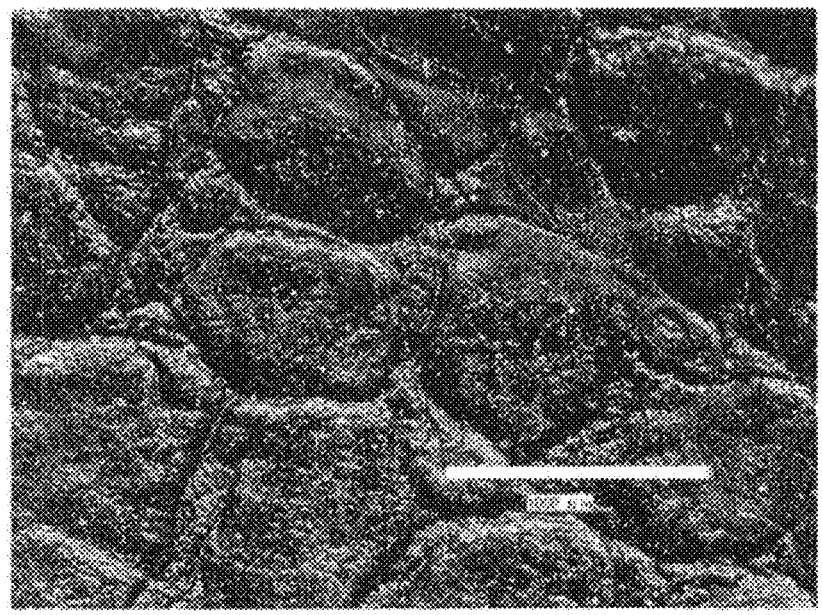
FIG. 4b is an enlarged view of the surface of the artificial leather to which the cosmetic composition of the present invention was applied and dried. In the figure, the white bar indicates a length of 1,000 µm.

Table 1 shows the results of evaluating the performance of the products of Examples 1 to 4 and Comparative Examples 1 to 3. In this table, the unit of the content of polyalkylene oxide-modified product "mass %" is "mass/mass %". FIG. 4a shows an enlarged photograph (×100 times) of the surface of the artificial leather itself used for the experiments. FIG. 4b shows an enlarged photograph (×100 times) of the surface of the artificial leather after rubbing the cosmetic composition of Example 2 into the surface of the artificial leather, followed by drying. As is clear from FIG. 4b, the grooves in the surface of the artificial leather are filled with the cosmetic composition and the surface thereof becomes smooth.

TABLE 1

| | Polymer 1) | | | Lower alcohol aqueous solution | | Sliding property (mean coefficient of friction) | | | | Stability Viscosity [mPa · s] | |
|---|---|---|---|---|---|---|---|---|---|---|---|
| | | | | | | Before durability test | | After durability test | | | |
| | Type | Median diameter [µm] | [Mass %] | Type of lower alcohol | Concentration [Mass %] | Value (MIU) | deviation (MMD) | Value (MIU) | deviation (MMD) | Before exposure | After exposure |
| Example 1 | Production Example 1 | 100 | 3 | — | — | 0.27 | 0.01 | 0.27 | 0.01 | 1,300 | 1,300 |
| Example 2 | Production Example 1 | 100 | 3 | Ethanol | 90 | 0.25 | 0.01 | 0.25 | 0.01 | 250 | 250 |
| Example 3 | Production Example 2 | 50 | 0.5 | Isopropanol | 65 | 0.29 | 0.01 | 0.29 | 0.01 | 250 | 250 |
| Example 4 | Production Example 2 | 50 | 1.5 | Propanol | 80 | 0.22 | 0.01 | 0.22 | 0.01 | 550 | 550 |
| Comp. Ex. 1 | Production Example 1 | 100 | 0.1 | — | — | 0.33 | 0.02 | 0.36 | 0.02 | 120 | 120 |
| Comp. Ex. 2 | Production Example 3 | 50 | 3 | Ethanol | 90 | 0.31 | 0.02 | 0.37 | 0.02 | 1,500 | 150 |
| Comp. Ex. 3 | Production Example 4 | 100 | 3 | Ethanol | 90 | 0.33 | 0.04 | 0.37 | 0.04 | 2,200 | 100 |

1) Production Examples 1 and 2: Polyalkylene oxide-modified product Production Example 3: Acrylate-based water-soluble polymer Production Example 4: Acrylate-based water-absorbable polymer As is clear from the results shown in Table 1, a cosmetic composition comprising a polyalkylene oxide-modified product in an amount of 0.3 mass % or more, a surface without stickiness after the application and excellent sliding characteristics can be obtained. More specifically, by the use of these cosmetic compositions, desirable silkiness and smoothness can be achieved. Furthermore, such excellent sliding characteristics can be stably maintained after washing with water.

The invention claimed is:

1. A cosmetic composition comprising:
   (i) a pulverized polyalkylene oxide-modified product obtained by reacting a polyalkylene oxide compound, a diol compound, and a diisocyanate compound; and
   (ii) water or a lower alcohol aqueous solution; the cosmetic composition comprising 0.3 to 7.5 mass % pulverized polyalkylene oxide-modified product,
   the cosmetic composition further comprising at least one member selected from the group consisting of glycerol, glycol, sorbitol, dipropylene glycol, and polyethylene glycol, wherein the pulverized polyalkylene oxide-modified product has a median diameter of 30 to 150 µm.

2. The cosmetic composition according to claim 1, wherein the polyalkylene oxide compound comprises at least one member selected from the group consisting of polyethylene oxide, polypropylene oxide, polybutylene oxide, ethylene oxide/propylene oxide copolymer, ethylene oxide/butylene oxide copolymer, propylene oxide/butylene oxide copolymer, and ethylene oxide/propylene oxide/butylene oxide copolymer.

3. The cosmetic composition according to claim 1, wherein the diol compound comprises at least one member selected from the group consisting of ethylene glycol, diethylene glycol, triethylene glycol, tetraethylene glycol, propylene glycol, dipropylene glycol, trimethylene glycol, 1,3-butanediol, 2,3-butanediol, 1,4-butanediol, 1,5-pentanediol, 1,6-hexanediol, and 1,9-nonanediol.

4. The cosmetic composition according to claim 1; wherein the diisocyanate compound comprises at least one member selected from the group consisting of 4,4'-diphenylmethane diisocyanate (MDI), 1,6-hexamethylene diisocyanate (HDI), dicyclohexylmethane-4,4'-diisocyanate (HMDI), 3-isocyanate methyl-3,5,5-trimethyl cyclohexyl isocyanate (IPDI), 1,8-dimethylbenzole-2,4-diisocyanate, and 2,4-tolylene diisocyanate (TDI).

5. The cosmetic composition according to claim 1, wherein the pulverized polyalkylene oxide-modified product has a water absorption capability of 10 to 40 g/g.

6. The cosmetic composition according to claim 1, wherein the pulverized polyalkylene oxide-modified product has a water elution amount of 10 to 40 mass %.

7. A cosmetic which comprises the cosmetic composition of claim 1.

\* \* \* \* \*